United States Patent
Lee et al.

(10) Patent No.: US 10,107,817 B2
(45) Date of Patent: Oct. 23, 2018

(54) OLIGOPEPTIDE SPECIFIC TO OVARIAN CANCER, POLYNUCLEOTIDE FOR ENCODING OLIGOPEPTIDE, TEST KIT FOR DETECTING OVARIAN CANCER AND METHOD FOR DETECTING OVARIAN CANCER

(71) Applicant: NATIONAL TSING HUA UNIVERSITY, Hsinchu (TW)

(72) Inventors: Gwo-Bin Lee, Hsinchu (TW); Lien-Yu Hung, Hsinchu (TW); Chih-Hung Wang, Hsinchu (TW); Chien-Yu Fu, Hsinchu (TW); Wen-Bin Lee, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 30 days.

(21) Appl. No.: 15/410,784

(22) Filed: Jan. 20, 2017

(65) Prior Publication Data
US 2018/0113136 A1   Apr. 26, 2018

(30) Foreign Application Priority Data
Oct. 20, 2016   (TW) .............................. 105133912 A

(51) Int. Cl.
*G01N 33/574* (2006.01)
*C07K 7/08* (2006.01)

(52) U.S. Cl.
CPC ......... *G01N 33/57449* (2013.01); *C07K 7/08* (2013.01)

(58) Field of Classification Search
None
See application file for complete search history.

(56) References Cited

FOREIGN PATENT DOCUMENTS

TW   I490230 B   7/2015

OTHER PUBLICATIONS

Yu-Jui Che et al., "An integrated microfluidic system for screening of phage-displayed peptides specific to colon cancer cells and colon cancer stem cells", Biomicrofluidics, published in Sep. 2015, vol. 9, issue 5, 14 pages, published by American Institute of Physics, United States.

Chih-Hung Wang et al., "Cancer Cell-Specific Oligopeptides Selected by an Integrated Microfluidic System from a Phage Display Library for Ovarian Cancer Diagnosis", Theranostics, published in Apr. 2015, vol. 5, No. 4, pp. 431-442, published by Ivyspring International Publisher, Australia.

*Primary Examiner* — Alana Harris Dent
(74) *Attorney, Agent, or Firm* — CKC & Partners Co., Ltd.

(57) ABSTRACT

The present disclosure relates to an oligopeptide which is highly specific to an ovarian cancer. The oligopeptide includes an amino acid sequence of SEQ ID NO: 1. The present disclosure also relates to a test kit including the oligopeptide for detecting ovarian cancer and an ovarian cancer detection method by using the oligopeptide.

2 Claims, 3 Drawing Sheets
(2 of 3 Drawing Sheet(s) Filed in Color)
Specification includes a Sequence Listing.

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Lys Arg Leu Thr Pro Leu Ser Pro Asp His Tyr Asp
1               5                   10

<210> SEQ ID NO 2
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 2
aagaggctga cccccctgag ccccgaccac tacgac                         36
```

OLIGOPEPTIDE SPECIFIC TO OVARIAN CANCER, POLYNUCLEOTIDE FOR ENCODING OLIGOPEPTIDE, TEST KIT FOR DETECTING OVARIAN CANCER AND METHOD FOR DETECTING OVARIAN CANCER

RELATED APPLICATIONS

This application claims priority to Taiwan Application Serial Number 105133912, filed Oct. 20, 2016, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-3444-US_SequenceListing", created on Feb. 22, 2017, which is 4,096 bytes in size.

BACKGROUND

Technical Field

The present disclosure relates to an oligopeptide, a test kit and a detection method. More particularly, the present disclosure relates to the oligopeptide specific to an ovarian cancer, the test kit for detecting the ovarian cancer and the method for detecting the ovarian cancer.

Description of Related Art

An ovary is a ductless reproductive gland that produces oocytes and secretes steroid hormones. Females have a pair of ovaries, held by a membrane beside the uterus on each side of the lower abdomen. Size of the ovary can vary with the menstrual cycle, and the ovary will gradually shrink after an amenorrhea.

Ovarian cancer is one of the most common gynecological cancers, and it has highest mortality rate among the gynecological cancers. The risk of ovarian cancer increases in postmenopausal women or a woman who is aged from 55 years old to 75 years old. Early detection of the ovarian cancer usually has a good cure rate. However, most of the ovarian cancers are not easily to be diagnosed due to their insignificant early symptoms. Only when the tumor enlarged in late stages which suppress the large intestine and result in conditions can the tumor be discovered. Most of the ovarian cancers are found in the third stage, thus the prognosis of ovarian cancer is poor. The mortality of the ovarian cancer accounts for a very high proportion of the gynecological cancers, and the 5-year survival rate in late stage ovarian cancer is only 20-50%.

Currently, clinical ovarian cancer detection method includes ultrasonic examination, such as transvaginal ultrasound and doppler ultrasound, and serum tumor makers, such as CA-125, lysophosphatidic acid (LPA), α-fetoprotein (α-FP), human chorionic gonadotropin (hCG), inhibin and mullerian inhibiting substance (MIS). However, the ovary with ovarian cancer is similar to a normal one in size and appearance, such the transvaginal ultrasound and the doppler ultrasound lack reliability. Besides, the serum tumor makers exhibit low specificity, and the clinical uses of the serum tumor makers are mainly in the post-operative tracking and early detection of recurrent tumors. Developing the serum tumor marker with high specificity for clinical application is necessary. Thus, the public still need a practice or an examination that can be used as early ovarian cancer screening so far, since it can not only serve as rapid detection for early stage ovarian cancer but also increase the survival rate of prognosis.

SUMMARY

According to one aspect of the present disclosure, an oligopeptide specific to an ovarian cancer is provided. The oligopeptide includes an amino acid sequence of SEQ ID NO: 1.

According to another aspect of the present disclosure, a polynucleotide is provided. The polynucleotide includes a nucleotide encoding an amino acid sequence of SEQ ID NO: 1.

According to another aspect of the present disclosure, a test kit for detecting an ovarian cancer is provided. The test kit includes an oligopeptide consisted of an amino acid sequence of SEQ ID NO: 1.

According to still another aspect of the present disclosure, a method for detecting an ovarian cancer includes steps as follows. A sample is provided. A binding step is provided, wherein the sample is contacted with an oligopeptide consisted of an amino acid sequence of SEQ ID NO: 1 and performed a binding reaction. A detecting step is provided to detect whether the sample has an oligopeptide-cancer cell complex.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
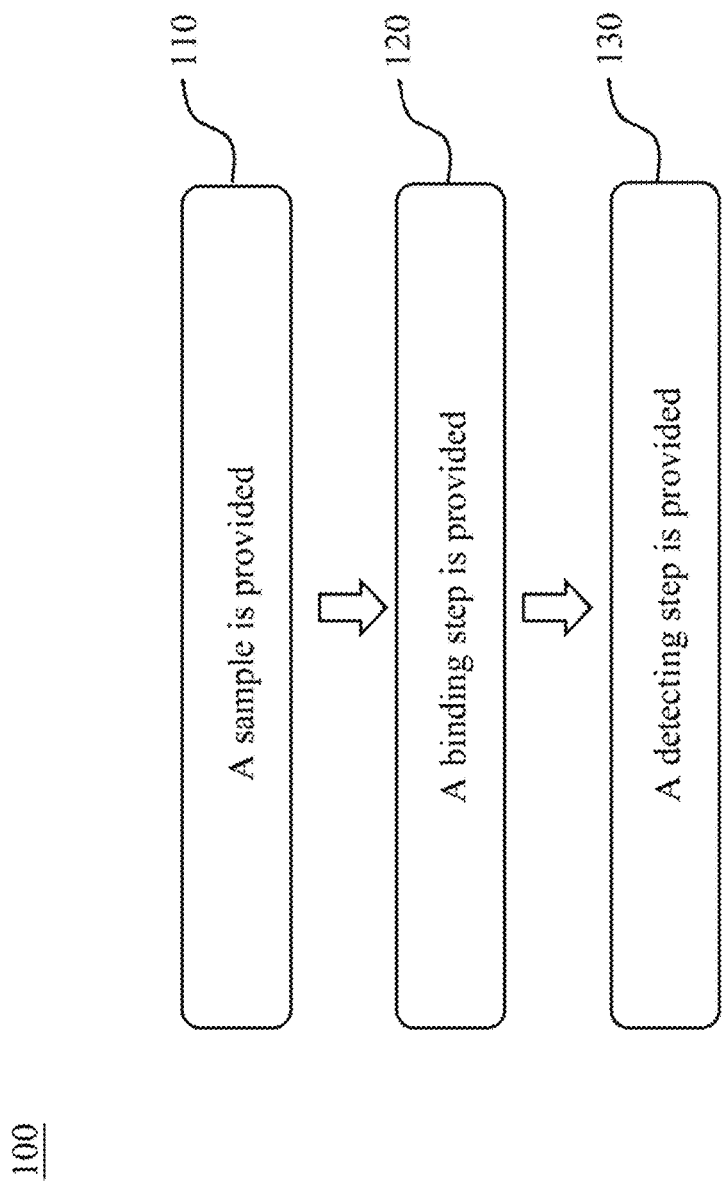
FIG. 1 is a flow diagram showing a method for detecting an ovarian cancer according to one embodiment of the present disclosure.

A novel oligopeptide, a polynucleotide encoding the oligopeptide, a test kit including the oligopeptide for detecting the ovarian cancer and a method for detecting the ovarian cancer by using the oligopeptide are provided. The oligopeptide is highly specific to the ovarian cancer. Further, the oligopeptide is mixed with different types of ovarian cancer tissues and ovarian cancer cells. The oligopeptide of the present disclosure specific binds to the ovarian cancer tissue or the ovarian cancer cells. It indicates that the oligopeptide of the present disclosure has specificity for the ovarian cancer, so that the oligopeptide of the present disclosure can be used for the early detection of the ovarian cancer.

Reference will now be made in detail to the present embodiments of the present disclosure, examples of which are illustrated in the accompanying drawings. Wherever possible, the same reference numbers are used in the drawings and the description to refer to the same or like parts.

EXAMPLES

I. The Oligopeptide of the Present Disclosure and the Polynucleotide Encoding the Oligopeptide The term "oligopeptide" refers to a short chain peptide consisted of two to twenty amino acids.

The term "polynucleotide" is a biopolymer composed of nucleotide monomers, as in deoxy ribonucleotides, ribonucleotides, and/or analogs or derivatives thereof, covalently bonded in a chain. The nucleotide sequence shown in the present disclosure is arranged in the 5' to 3' direction.

The amino acid sequence of the oligopeptide of the present disclosure includes is referenced as SEQ ID NO: 1, the oligopeptide is specific to the ovarian cancer. The nucleotide sequence of the polynucleotide which encodes the oligopeptide of the present disclosure can be referenced as SEQ ID: NO. 2. However, the same amino acids may be translated by different codons; person having ordinary skill in the art can design the polynucleotide encoding the oligopeptide of the present disclosure according to the amino acid sequence of the oligopeptide. Thus, any nucleotide sequence encoding the oligopeptide of the present disclosure will not depart from the scope of the present disclosure.

The oligopeptides of the present disclosure can be prepared using methods known in the art, including a cell-based protein expression system, a cell-free protein expression system, or a chemical synthesis to produce the oligopeptide of the present disclosure. Host cells of the cell-based protein expression system include bacteria, yeasts, fungi, plants, insects and mammalian cells.

II. The Test Kit for Detecting the Ovarian Cancer of the Present Disclosure

The test kit for detecting an ovarian cancer of the present disclosure includes the oligopeptide consisted of the amino acid sequence of SEQ ID NO: 1. The oligopeptide can be conjugated to a detectable label. The terms "detectable label" refer to a substance that can be covalently bound to or physically adsorbed to the oligopeptide of the present disclosure, thus the detectable label can be used to detect the presence of the oligopeptide. The detectable label can be a fluorophore, a chemiluminophore, a radioactive isotope, an enzyme, or a biotin. Further, the fluorophore can be, but not limit to, fluorescent groups such as FAM, JOE and VIC. The chemiluminophore can be, but not limit to, electro chemiluminescent compounds or chemiluminescent compounds, such as luminol, isoluminol or acridinium salts. The radioactive isotope can be, but not limit to, $^3H$, $^{14}C$, $^{32}P$, $^{35}S$, $^{125(131)}I$ and $^{75}Se$. The enzyme can be, but not limit to, enzymes having detectable products such as luciferase, peroxidase, alkaline phosphatase, β-galactosidase, and the analogs.

III. The Method for Detecting the Ovarian Cancer of the Present Disclosure

The method for detecting the ovarian cancer of the present disclosure is used for in vitro detection of the ovarian cancer, wherein aforementioned oligopeptide or aforementioned test kit can be used in the method. The oligopeptide consisted of the amino acid sequence of SEQ ID NO: 1 is contacted with a sample to detect whether the sample has an oligopeptide-cancer cell complex, wherein the oligopeptide-cancer cell complex represents a presence of the ovarian cancer.

FIG. 1 is a flow diagram showing the method 100 for detecting the ovarian cancer according to one embodiment of the present disclosure. The method 100 for detecting the ovarian cancer includes a step 110, a step 120 and a step 130.

In the step 110, the sample is provided, wherein the sample is obtained from a subject. The sample can be a frozen tissue section, a paraffin-embedded tissue section or a tissue microarray.

In the step 120, a binding step is provided, wherein the sample is contacted with the oligopeptide consisted of the amino acid sequence of SEQ ID NO: 1 and performed a binding reaction. The oligopeptide can be conjugated to the detectable label, and the detectable label can be the fluorophore, the chemiluminophore, the radioactive isotope, the enzyme, or the biotin.

In the step 130, a detecting step is provided to detect whether the sample has the oligopeptide-cancer cell complex. When the oligopeptide-cancer cell complex is detected in the sample, the subject who provides the sample suffers from the ovarian cancer. The term "oligopeptide-cancer cell complex" refers to a complex formed by the oligopeptide of the present disclosure binding to the ovarian cancer cell. The oligopeptide-cancer cell complex can be detected by an immunofluorescence, an immunohistochemistry, a Western blot, an enzyme-linked immunosorbent assay (ELISA) or an autoradiography.

In subsequent examples, the oligopeptide of the present disclosure is used to detect whether the sample has the oligopeptide-cancer cell complex. The oligopeptide consisted of the amino acid sequence of SEQ ID NO: 1 is chemically synthesized and modified a green fluorescence (FAM) at N-terminus in subsequent examples.

3.1 the Specificity of the Oligopeptide of the Present Disclosure to the Ovarian Cancer Tissue The sample uses in this example is the ovarian cancer tissue including an ovarian serous tumor tissue section, an ovarian mucinous tumor tissue section and an ovarian clear cell carcinoma tissue section. Besides, a normal ovarian tissue section is used as a control. The oligopeptide modified with the green fluorescence is respectively mixed with different groups of the sample at 60 rpm for 60 minutes at room temperature. The samples are washed several times with PBS containing 1% BSA. Then the sample is observed under a fluorescence microscopy, wherein the green fluorescent signal represents that the oligopeptide-cancer cell complex is presented in the sample.

Figure 2:
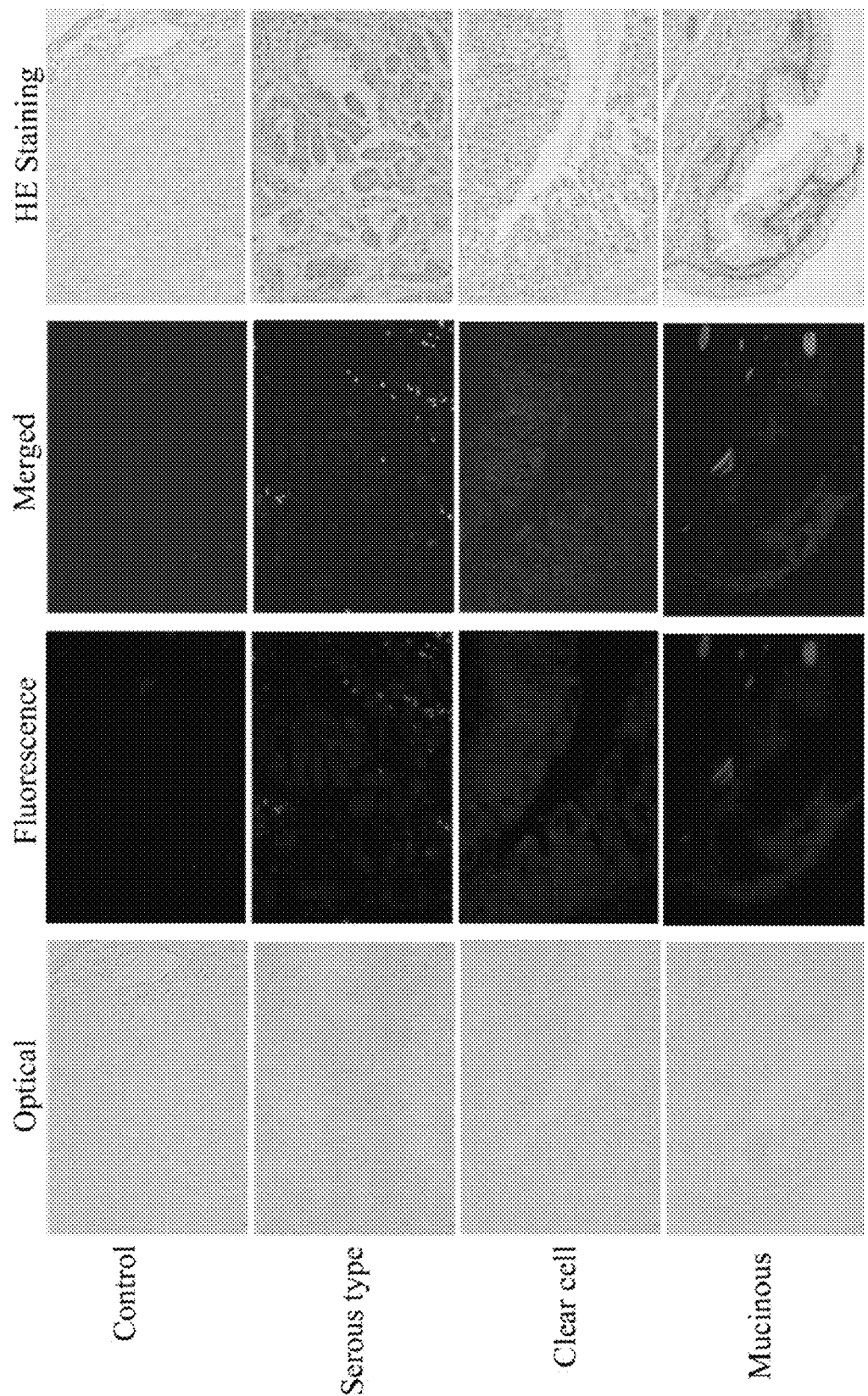
FIG. 2 shows analytical results of ovarian cancer tissues detected by an oligopeptide of the present disclosure.

FIG. 2 shows analytical results of the ovarian cancer tissues detected by the oligopeptide of the present disclosure. In FIG. 2, there is no significant green fluorescent signal detected in the control. However, the green fluorescent signal can be detected in different ovarian cancer tissue sections, including the ovarian serous tumor tissue section, the ovarian mucinous tumor tissue section and the ovarian clear cell carcinoma tissue section. It indicates that the oligopeptide of the present disclosure has high specificity for the ovarian cancer tissue and has high specificity for different types of the ovarian cancer tissues.

3.2 the Specificity of the Oligopeptide of the Present Disclosure to Ovarian Cancer Cells The sample uses in this example is the ovarian cancer cell, wherein the ovarian cancer cell is OVCAR3 cell (a human serous epithelial ovarian cancer cell line). Besides, a normal cervical epithelial cell is used as the control. The OVCAR3 cell and the normal cervical epithelial cell are cultured and stored in Department of Obstetrics and Gynecology of National Cheng Kung University Hospital. The OVCAR3 cell and the normal cervical epithelial cell are respectively seeded in a 12-well plate with $1 \times 10^5$ cells/well and then maintained at 37° C. in a humidified atmosphere of 5% $CO_2$ until the cells are adhered in the next day. The oligopeptide modified with the green fluorescence is respectively mixed with different groups of the sample at 60 rpm for 60 minutes at room temperature. The sample is washed several times with the PBS containing 1% BSA. Then the sample is observed under a fluorescence microscopy, wherein the green fluorescent signal represents that the oligopeptide-cancer cell complex is presented in the sample.

Figure 3:
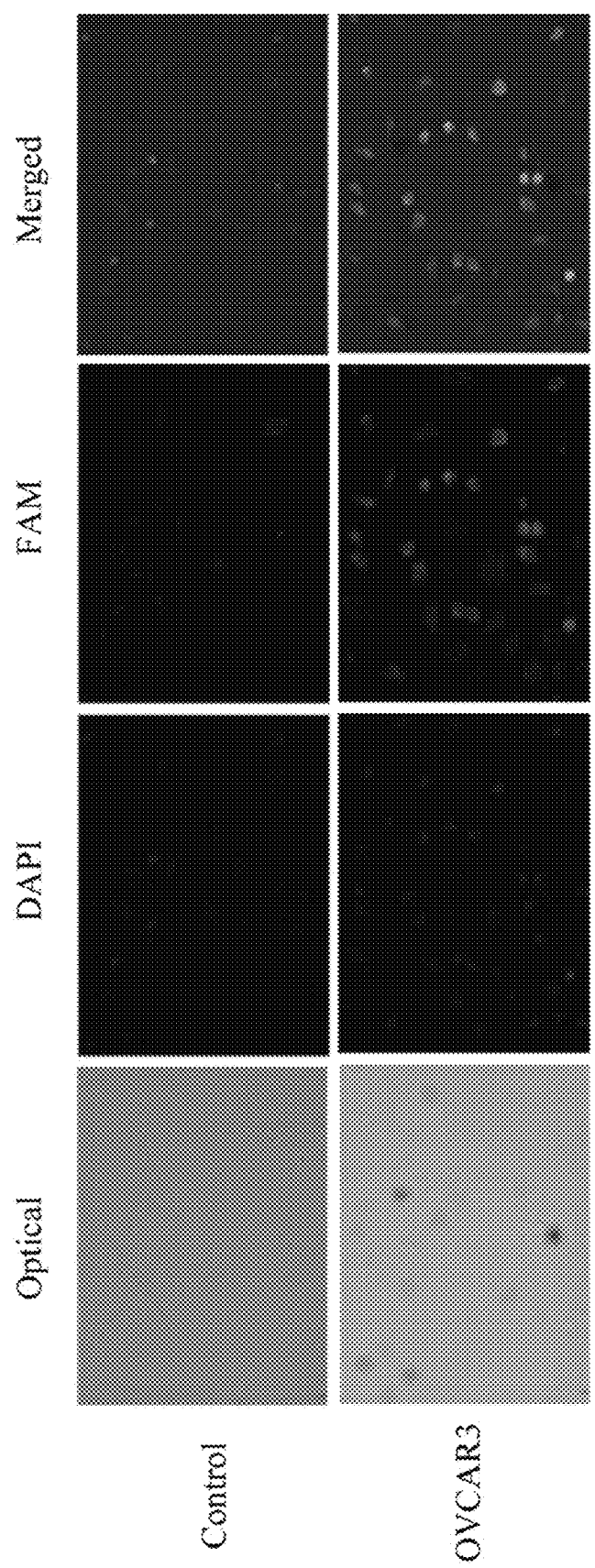
FIG. 3 shows analytical results of the ovarian cancer cells detected by the oligopeptide of the present disclosure.

FIG. 3 shows analytical results of the ovarian cancer cells detected by the oligopeptide of the present disclosure, wherein DAPI signal represents the location of the nucleus, and FAM signal represents the location of the oligopeptide-cancer cell complex. In FIG. 3, there is no significant FAM signal detected in the control. However, the FAM signal can be detected in the OVCAR3 cell. It indicates that the oligopeptide of the present disclosure has high specificity for the ovarian cancer cell.

To sum up, the novel oligopeptide and the polynucleotide encoding the oligopeptide are provided in the present disclosure. The oligopeptide has high specificity for the ovarian cancer tissue and the ovarian cancer cell, in particular the ovarian serous tumor, the ovarian mucinous tumor and the ovarian clear cell carcinoma. Therefore, the oligopeptide of the present disclosure can be an ideal tool for early detection of the ovarian cancer. The test kit including the oligopeptide and the method for detecting the ovarian cancer by using the oligopeptide are provided can rapidly and accurately detect the ovarian cancer at an early stage for improving a cure rate and a survival rate of ovarian cancer patients. Therefore, the test kit and the method for detecting the ovarian cancer of the present disclosure can solve the problem that none of the tests and examinations so far can effectively early detect the ovarian cancer.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An isolated oligopeptide specific to an ovarian cancer, comprising the amino acid sequence of SEQ ID NO: 1.

2. The oligopeptide specific to the ovarian cancer of claim 1, wherein the ovarian cancer is an ovarian serous tumor, an ovarian mucinous tumor or an ovarian clear cell carcinoma.

* * * * *